US010265350B2

(12) United States Patent
Rubio Nistal et al.

(10) Patent No.: US 10,265,350 B2
(45) Date of Patent: Apr. 23, 2019

(54) PROBIOTIC AND PREBIOTIC COMPOSITIONS

(71) Applicants: AQUILÓN CYL S.L, León (ES); UNIVERSIDAD DE LEÓN, León (ES)

(72) Inventors: Pedro Miguel Rubio Nistal, Leon (ES); Ana María Carvajal Urueña, Leon (ES); Marta García Díez, Leon (ES)

(73) Assignees: UNIVERSIDAD DE LEON, Leon (ES); AQUILON CYL SOCIEDAD LIMITADA, Leon (ES)

( * ) Notice: Subject to any disclaimer, the term of this patent is extended or adjusted under 35 U.S.C. 154(b) by 237 days.

(21) Appl. No.: 14/430,962

(22) PCT Filed: Sep. 25, 2013

(86) PCT No.: PCT/EP2013/070017
§ 371 (c)(1),
(2) Date: Mar. 25, 2015

(87) PCT Pub. No.: WO2014/049023
PCT Pub. Date: Apr. 3, 2014

(65) Prior Publication Data
US 2015/0250833 A1    Sep. 10, 2015

(30) Foreign Application Priority Data

Sep. 25, 2012    (EP) .................................... 12382373

(51) Int. Cl.
*C12R 1/225* (2006.01)
*A61K 45/00* (2006.01)
(Continued)

(52) U.S. Cl.
CPC ............ *A61K 35/744* (2013.01); *A23K 10/18* (2016.05); *A23K 20/163* (2016.05); *A23K 50/30* (2016.05);
(Continued)

(58) Field of Classification Search
None
See application file for complete search history.

(56) References Cited

U.S. PATENT DOCUMENTS 5,478,559 A    12/1995    Yabiki et al.
5,800,813 A    9/1998    Casas
(Continued)

FOREIGN PATENT DOCUMENTS

CN    102304489 A    1/2012
EP    0199535 A2    10/1986
(Continued)

OTHER PUBLICATIONS

De Vrese et al. "Probiotics and Prebiotics: Effects on Diarrhea" Journal of Nutrition Effects of Probiotics and Prebiotics, Supplement 803S-811S, 2007.*
(Continued)

*Primary Examiner* — Blaine Lankford
*Assistant Examiner* — Lauren K Van Buren
(74) *Attorney, Agent, or Firm* — McCarter & English LLP; Jill Ann Mello

(57) ABSTRACT

The invention relates to products and compositions that may be beneficial in animal husbandry. Said products and compositions comprise microorganisms, such as bacteria, and probiotic bacteria in particular. Thus, provided herein are microbial strains, as well as selection criteria which will enable the skilled reader to find further strains useful in the present invention. The strains, as well as compositions comprising the same, may be administered to animals, farmed animals such as swine in particular. The administration may occur in the first days of life. By administration of the products or compositions of the inventions animal growth can be promoted and animal weight can be increased. Bacterial infections may also be prevented or treated by said compounds or compositions.

24 Claims, 1 Drawing Sheet

(51) Int. Cl.
     A61K 35/66        (2015.01)
     A61K 35/74        (2015.01)
     C12N 1/20         (2006.01)
     A61P 1/12         (2006.01)
     A61P 31/04        (2006.01)
     A61K 35/744       (2015.01)
     C12R 1/46         (2006.01)
     A61K 45/06        (2006.01)
     A23K 10/18        (2016.01)
     A23K 20/163       (2016.01)
     A23K 50/30        (2016.01)
     A23L 33/135       (2016.01)
     A23L 33/21        (2016.01)

(52) U.S. Cl.
     CPC .......... A23L 33/135 (2016.08); A23L 33/21
           (2016.08); A61K 45/06 (2013.01); C12R 1/225
                       (2013.01); C12R 1/46 (2013.01)

(56)             References Cited

U.S. PATENT DOCUMENTS 5,849,289 A  * 12/1998 Dobrogosz .......... C07D 319/06
                                                      424/93.45
     2006/0039899 A1    2/2006 Winn
     2007/0098705 A1 *  5/2007 Ljungh-Wadstrom ......................
                                                       A61K 35/744
                                                        424/93.45
     2017/0035815 A1 *  2/2017 Kim ................... A61K 35/747

FOREIGN PATENT DOCUMENTS

EP         1808081 A1      7/2007
     JP       11-141435 A       5/1999
     JP      2004-523241 A      8/2004
     JP      2006-101784 A      4/2006
     RU         2372788 C2     11/2009
     WO       1995/33046 A1    12/1995
     WO       2001/90311 A1    11/2001
     WO       2002/43649 A2     6/2002
     WO    WO-2005/074626 A2    8/2005
     WO    WO-2005/095656 A1   10/2005
     WO       2006/040816 A1    4/2006
     WO      WO2011007922   *   1/2011

OTHER PUBLICATIONS

De Keersmaecker, S.C.J. et al., "Strong antimicrobial activity of *Lactobacillus rhamnosus* GG against *Salmonella typhimurium* due to accumulation of lactic acid," *FEMS Microbiology Letters*, vol. 259, pp. 89-96, 2006.
De Vrese, M. and Marteau, P.R.., "Probiotics and Prebiotics: Effects on Diarrhea," *The Journal of Nutrition*, vol. 137, pp. 803S-811S, 2007.
García-Almendárez, B. E. et al., "Effect of *Lactococcus lactis* UQ2 and its bacteriocin on *Listeria monocytogenes* biofilms," *Food Control*, vol. 19, No. 7, pp. 670-680, 2008.
International Search Report and Written Opinion for PCT/EP2013/070017 dated Dec. 6, 2013.
Maragkoudakis, P. A. et al., "Probiotic potential of *Lactobacillus* strains isolated from dairy products," *International Dairy Journal*, vol. 16, pp. 189-199, 2006.
Oh, S. et al., "Characterization and Purification of a Bacteriocin Produced by a Potential Probiotic Culture, *Lactobacillus acidophilus* 30SC," *Journal or Dairy Science*, vol. 83, No. 12, pp. 2747-2752.
Razdan, K. et al., "Isolation and Characterization of a Lipolyctic and Phytase Producing Probiotic for Potential Application in Poultry Feed," *Online Journal of Animal and Feed Research*, vol. 2, No. 4, pp. 369-377, 2011.
Sim, K. Y. et al., "Probiotic Potential and Antimicrobial Activities of Micro-Organisms Isolated from an Indigenous Fish Sauce," *Borneo Science*, vol. 31, pp. 49-55, 2012.
Songer, Glenn J., "Clostridiosis," *Diseases of Swine*, Tenth Edition, Editors: Zimmerman, J. J. et al., pp. 709-712, 714-715, 728-729, 731-733, 2012.
Meira et al., Probiotic potential of *Lactobacillus* spp. isolated from Brazilian regional ovine cheese. J Dairy Res. Feb. 2012;79(1):119-27.
Abe et al., Effect of Administration of Bifidobacterium and Lactic Acid Bacteria to Newborn Calves and Piglets. Journal of Dairy Science. Dec. 1995;78(12):2838-2846.
Gaggía et al., Probiotics and prebiotics in animal feeding for safe food production. Int J Food Microbiol. Jul. 31, 2010;141 Suppl 1:S15-28.
Prasad et al., Selection and Characterisation of Lactobacillus and Bifidobacterium Strains for Use as Probiotics. International Dairy Journal. Dec. 1998;8(12):993-1002.
Rivas et al., Antibacterial potential of Enterococcus faecium strains isolated from ewes' milk and cheese. LWT—Food Science and Technology. 2012;46:428-436.
Zeyner et al., Effects of a probiotic Enterococcus faecium strain supplemented from birth to weaning on diarrhoea patterns and performance of piglets. J Anim Physiol Anim Nutr (Berl). Feb. 2006;90(1-2):25-31.

* cited by examiner

PROBIOTIC AND PREBIOTIC COMPOSITIONS

RELATED APPLICATIONS

This application is a 35 U.S.C. § 371 national stage filing of International Application No. PCT/EP2013/070017, filed Sep. 25, 2013, which claims priority to European Patent Application No. 12382373.4, filed Sep. 25, 2012. The entire contents of each of the foregoing applications are incorporated herein by reference.

BACKGROUND ART

Newborn animals and those in (intense) farming in particular, are prone to bacterial and other infections. These infections can lead to diarrhoea associated with weight loss and, in severe cases, even to death of the newborn. For example, several years ago, diarrhoeal cases in newborn piglets have been described in swine farms from different geographical situations in Spain. It is believed that said diarrhoea is a symptom in these animals, whereas the causative factor of said symptom is sometimes difficult to locate. In many cases of diarrhoea in newborn swine for example, it is possible to isolate possibly unfavorable/undesired bacterial strains, such as *Escherichia coli*, alone or in combination with *Clostridium perfringens* or *Clostridium difficile*, but diarrhoea is usually detected just after birth and routine treatment and prophylaxis procedures are oftentimes not effective.

Without wishing to be bound to any particular theory, it is believed that dysbiosis (also called dysbacteriosis) may be a causative factor. Dysbiosis refers to a condition with microbial imbalances on or within the body. In farming animals, swine in particular, dysbiosis may be caused by indiscriminate use of antibiotics during sow maintenance, producing alterations in newborn piglet's intestinal flora.

In view of these disadvantages of the use of antibiotics, it is recommended to reduce the use of antibiotics in animal husbandry. On the other hand, alternative methods of treatment of the newborn animals would then be required to replace the commonly used antibiotics.

Since the EU recommends since 2005 to reduce the use of antibiotics as growth promoters in swine breading (Amended by Regulation (EC) No 378/2005 of 4 Mar. 2005), animal breeders are longing for alternatives which can improve the general health status of (farm) animals, particularly in the early days of life. The present inventors provide a solution to this problem, and said solution is described in the following. The present invention thus solves several problems caused by state of the art methods, and the advantageous effects will be detailed below.

BRIEF DESCRIPTION OF THE INVENTION

In a first aspect, the invention relates to a composition comprising at least one, such as one, preferably at least two, such as two, more preferably at least three, such as three, more preferably at least four, such as four, alternatively at least five, such as five, alternatively at least six, such as six, alternatively at least seven, such as seven, alternatively at least eight, such as eight microorganism(s), preferably a bacterium, and more preferably a lactic acid bacterium. The lactic acid bacterium is ideally selected from the following strains: CECT 8163 (AqSyn04); CECT 8165 (AqSyn06); CECT 8164 (AqSyn09); CECT 8166 (AqSyn10), CECT 8347 (AqSynJ12); CECT 8348 (AqSynJ17); CECT 8349 (AqSynJ55) and CECT 8350 (AqSynJ59), which were all deposited with CECT.

In one embodiment, the composition comprising one or more strains, wherein each strain fulfills at least the following condition a., and preferably both conditions a. and b., and most preferably all conditions a., b. and c.:
a. shows an antimicrobial activity evidenced by at least one of the following inhibition zones: (i) 10 mm or more, for example 14 mm or more, for *Salmonella*, (ii) 9 mm or more, preferably 10 mm or more, for *Listeria monocytogenes*, (iii) 9 mm or more, preferably 10 mm or more, for *Staphyloccocus aureus*, (iv) 10 mm or more, for example 18 mm or more, for *Escherichia coli*;
b. is able to retain essentially the same viability during 3 hours of incubation at pH=3.5, or, alternatively at pH=2.5;
c. is able to retain essentially the same viability during 4 hours of incubation in presence of 0.45% bile extract, preferably at pH=8.

The composition of the invention may be for use in a method for treating or preventing the diarrhoea caused by a bacterial infection, and/or for increasing weight of a newborn mammal (preferably a piglet). In this method the composition is administered to the mammal.

The invention also provides a microorganism, preferably a bacterium, and more preferably a lactic acid bacterium. The lactic acid bacterium is ideally selected from the following strains: *Lactobacillus reuteri* strain CECT 8163 (AqSyn04); *Lactobacillus reuteri* strain CECT 8165 (AqSyn06); *Enterococcus faecium* strain CECT 8164 (AqSyn09); *Enterococcus faecium* strain CECT 8166 (AqSyn10), *Lactobacillus fermentum* strain CECT 8347 (AqSynJ12); *Lactobacillus reuteri* strain CECT 8348 (AqSynJ17); *Lactobacillus mucosae* strain CECT 8349 (AqSynJ55) and *Lactobacillus plantarum* strain CECT 8350 (AqSynJ59), which were all deposited with CECT (Spanish Type Cultures Collection; Edificio 3 CUE, Parc Científic Universitat de Valencía, Catedrático Agustín Escardino, 9, 46980 Paterna (Valencia), Spain) by AQUILON CYL S.L.

AqSyn numbers in brackets, which can be used synonymously for each of the strains, were allocated to the strains by the present inventors.

CECT 8163 (AqSyn04); CECT 8165 (AqSyn06); CECT 8164 (AqSyn09) and CECT 8166 (AqSyn10) were deposited on Jun. 20, 2012. CECT 8347 (AqSynJ12); CECT 8348 (AqSynJ17); CECT 8349 (AqSynJ55) and CECT 8350 (AqSynJ59) were deposited on May 16, 2013.

In a particular embodiment, the composition comprises at least one, such as one, preferably two, such as two, more preferably at least three, such as three of the following three strains: CECT 8163 (AqSyn04); CECT 8164 (AqSyn09) and CECT 8166 (AqSyn10). In an alternative embodiment, the composition comprises all four of CECT 8163 (AqSyn04); CECT 8165 (AqSyn06); CECT 8164 (AqSyn09); and CECT 8166 (AqSyn10).

In an alternative embodiment, the composition comprises one or more of CECT 8163 (AqSyn04); CECT 8165 (AqSyn06); CECT 8164 (AqSyn09); CECT 8166 (AqSyn10); CECT 8347 (AqSynJ12); CECT 8348 (AqSynJ17); CECT 8349 (AqSynJ55) and CECT 8350 (AqSynJ59), such as one, two, three, four, five, six seven, eight.

In an alternative embodiment, the composition comprises at least one, such as one, preferably at least two, such as two, more preferably at least three, such as three, more preferably at least four, such as four of CECT 8347 (AqSynJ12); CECT 8348 (AqSynJ17); CECT 8349 (AqSynJ55) and CECT 8350 (AqSynJ59).

In an alternative embodiment, the composition comprises the following three strains: CECT 8347 (AqSynJ12); CECT 8348 (AqSynJ17) and CECT 8349 (AqSynJ55). In an alternative embodiment, the composition comprises the following three strains: CECT 8348 (AqSynJ17); CECT 8349 (AqSynJ55) and CECT 8350 (AqSynJ59). In an alternative embodiment, the composition comprises the following three strains: CECT 8347 (AqSynJ12); CECT 8348 (AqSynJ17); and CECT 8350 (AqSynJ59). In an alternative embodiment, the composition comprises the following three strains: CECT 8347 (AqSynJ12); CECT 8349 (AqSynJ55) and CECT 8350 (AqSynJ59). In a preferred embodiment, the composition comprises all four of CECT 8347 (AqSynJ12); CECT 8348 (AqSynJ17); CECT 8349 (AqSynJ55) and CECT 8350 (AqSynJ59).

In one embodiment of the present invention at least one of the strains comprised in the composition, such as one, and/or two, and/or three, and/or four and/or five, and/or six, and/or seven and/or eight, and preferably all of the strains comprised in the composition, are free from antibiotic resistance, namely they are not able to survive after exposure to the appropriate standard antibiotic treatment.

In either case "comprises" may optionally be understood in that further bacterial strains are present, or that no further bacterial strains are present. Even if no further bacterial strains are present, "comprises" may optionally mean that further other ingredients, i.e. any ingredients other than bacteria are present.

The other ingredient (or other ingredients) is not limited in any way. In a preferred aspect, at least one prebiotic compound is comprised in the composition of the invention, i.e. as other ingredient.

Concerning the compositions of different strains, any mixing ratio is possible. The mixing ratio is indicated in the following by colony forming units (CFU), the CFU are suitably determined prior to mixing the individual strains. In one embodiment, the ratios of the strains may or may not be equal, such as 1:(0,1-10):(0,1-10) for a composition of three strains, 1:1:(0,1-10):(0,1-10):(0,1-10) for a composition of four strains, and so forth. In another embodiment, the ratios of the strains are roughly or substantially equal, such as 1:1:1 for a composition of three strains and 1:1:1:1 for a composition of four strains, and so forth. The composition can be prepared by mixing the respective bacterial amount (as determined by colony count) of each strain to be incorporated into the composition. The strains to be incorporated may be provided as stocks of individual strains, each one of them for example in the form of a lyophilisate. In the event that different stocks have different concentrations (CFU/g), appropriate amounts (g) of each one are used, so that the desired composition has the desired CFU of each of the strains. Examples thereof are shown below.

Prebiotics are well known in the art and when used in the present invention there is no particular limitation of the prebiotic as such. In preferred embodiments however the at least one prebiotic product in the composition is selected from the following compounds and compositions: beta-glucans, mannan-oligosaccharides, inulin, oligofructose, galactooligosaccharides (GOS), lactulose, lactosucrose, galactotriose, fructo-oligosaccaride (FOS), cellobiose, cellodextrins, cylodextrins, maltitol, lactitol, glycosilsucrose, Vitamin E or a variant thereof (wherein the variants are selected from alfa, beta, gamma, delta tocoferols, tocotrienols and tocomonoenols). Optionally, mannan-oligosaccharides and/or inulin may be preferred.

The present invention also provides the use of the composition described above in a method of treating a human or animal. Treatment of an animal, a mammal and/or a domestic animal in particular, may be preferred. Preferably, the animal is a non-human animal, and more preferably it is from the suborder Suina (the suborder Suina (also known as Suiformes) are a lineage of mammals that includes the pigs and peccaries of the families Suidae and Tayassuidae). Swine or pig, either wild or domestic, may be particularly preferred. In another embodiment the composition is administered to a human.

The invention also provides a composition comprising microorganisms, preferably bacteria, and more preferably lactic acid bacteria for use in a method for treating or preventing the diarrhoea caused by a bacterial infection, and/or for increasing weight of a newborn mammal, preferably a piglet. Alternatively, the composition is for use in a method for promoting growth of a newborn mammal, preferably a piglet.

Said composition for use in a method for treating or preventing the diarrhoea caused by a bacterial infection, and/or for increasing weight and/or for promoting growth may comprise at least one of the bacterial strains CECT 8163 (AqSyn04); CECT 8165 (AqSyn06); CECT 8164 (AqSyn09); CECT 8166 (AqSyn10); CECT 8347 (AqSynJ12); CECT 8348 (AqSynJ17); CECT 8349 (AqSynJ55) and CECT 8350 (AqSynJ59). In some embodiments said composition for use in a method for treating or preventing the diarrhoea caused by a bacterial infection, and/or for increasing weight and/or for promoting growth is the above-described particular composition (in any embodiment described).

The composition for the use in a method for treating or preventing the diarrhoea caused by a bacterial infection, and/or for increasing weight and/or for promoting growth may be administered within the first 14 days after birth (more preferably within the first 13, 12, 11, 10, 9, 8, 7, 6, 5, 4, 3 or 2 days after birth and most preferably within the first 2 days after birth or within the first 1 day (24 hours) after birth.

To that end, the composition may be administered orally, for example. The composition may be in any form, such as in lyophilized, liquid or nebulized form. If for example lyophilized bacteria are used for making the composition, then said preliminary composition of lyophilized bacteria may be rehydrated, e.g. with sterile isotonic saline solution, so that a final composition with the desired total concentration (CFU/ml) can be obtained.

To provide for easy use, the composition may be in dosed form. For example, each dose comprises $10^7$ or more, $10^8$ or more, $10^9$ or more, $10^{10}$ or more, $10^{11}$ or more colony forming units (CFU) of bacteria ($10^9$ or more may be preferred). A dose may have a volume in the range of 0.1 to 100 ml, preferably 0.2 to 50 ml, more preferably 0.5 to 20 ml, more preferably 1.0 to 10 ml, more preferably 1.5 to 5 ml, and even more preferably (substantially) 2 ml. A 2 ml dose with $10^9$ or more CFU may be particularly preferred.

Any number of doses may be administered and the skilled person can chose the length of the treatment according to the needs at the respective farm. In a particular embodiment the total number of doses administered to an animal is 10 or less, such as any number selected from the following: 1, 2, 3, 4, 5, 6, 7, 8, 9, 10, or any range combining any one of these numbers (except 10) with any one of these number, provided that the second number is higher (e.g. 1 to 3 doses for example). A total of two doses per animal may be particularly preferred.

In a preferred embodiment, a first dose is administered in the first 24 hours after birth and a second dose is administered in the subsequent 24 hours. Optionally, these are the only two doses. In another option, further doses are administered in the following.

The composition of the invention is particularly suitable for treating or preventing a condition in a mammal, such as a bacterial infection. In some embodiments the condition may be selected from diarrhoea due to bacterial infections (including collibacilosis), *Clostridium difficile* newborn diarrhoea, *Clostridium perfringens* A and C type. It is also possible to administer the composition to animals suffering from diarrhoea, even if a (bacterial) infection has not (yet) been proven to be the causative factor for said diarrhoea.

DETAILED DISCLOSURE OF THE INVENTION

Figure 1:
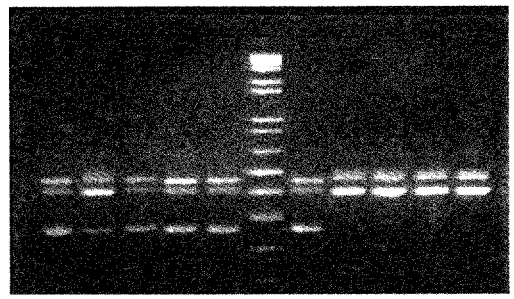
FIG. 1: Different PCR patterns usually aim at distinctive bacterial species as described in Example 1 (lanes 1-5, 7: *Lactobacillus reuteri*, lanes 8-11: *Enterococcus faecium*, lane 6: Molecular weight Marker).
Figure 2:
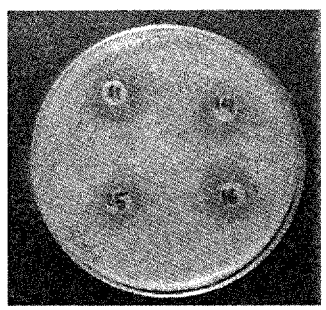
FIG. 2: Inhibition zones, illustrative example.

The following detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

Unless expressly specified otherwise, the term "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Unless expressly specified otherwise, all indications of relative amounts in the present application are made on a weight/weight basis. Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

The present invention integrates the concept of probiotics and prebiotics, thereby providing synbiotics. The inventors open a new therapeutic window of bacteria and compositions having an immune modulator effect. The microorganisms or compositions may be administered at an early life stage of an animal, such as a piglet. Thus, the invention relates to products and compositions that may be beneficial in animal husbandry. The real important observation, as evidenced by the examples, is that the probiotic treatment is at least equally effective, and most probably better (compared to standard antibiotic treatment), in terms of productivity to the treatment with antibiotics. The inventors' contribution has a huge economic impact both because of the overall cost of treatment and because of legal pressure and environmental impact The microorganisms, preferably bacteria that can be used according to the invention are microorganisms with beneficial effects. They preferably are lactic acid bacteria. Even non-bacterial species of microorganisms can be used according to the present invention, as long as they comply with the selection criteria a. to c. below. For example, it is known that some yeasts can have probiotic properties too.

Although the functional parameters described herein are the most important selection criteria, as far as species of the microorganisms are concerned, lactic acid bacteria are preferred. Lactic acid bacteria (LAB) comprise a clade of Gram-positive, acid-tolerant bacteria that are associated by their common metabolic and physiological characteristics. These bacteria, naturally found in decomposing plants and lactic products, as well as in animal feces, produce lactic acid as a major metabolic end-product of carbohydrate fermentation. Lactic acid bacteria are generally recognized as safe (GRAS status), due to their ubiquitous appearance in food and their contribution to the healthy microflora of mammalian mucosal surfaces. Lactic acid bacteria are preferably selected among the genera *Lactobacillus, Leuconostoc, Pediococcus, Lactococcus, Streptococcus Aerococcus, Carnobacterium, Enterococcus, Oenococcus, Sporolactobacillus, Tetragenococcus, Vagococcus,* and *Weisella. Lactobacillus* and/or *Enterococcus* may be preferred. *Lactobacillus* is preferred. The bacteria preferred herein are preferably Gram positive and are catalase negative. Whether a bacterium is Gram positive can be tested according to standard technologies known in the art. Gram staining consists in consecutive staining with different "colorings" (stains) and washing of the sample in order to check if it is positive or negative. Whether a bacterium is catalase negative is tested as follows: The catalase test involves adding hydrogen peroxide to a culture sample or agar slant. If the bacteria in question produce catalase, they will convert the hydrogen peroxide and oxygen gas will be evolved. The evolution of gas causes bubbles to form and these bubbles are indicative of a positive test (catalase positive bacterium).

The lactic acid bacteria preferred herein are preferably able to grow in MRS medium, and more preferably in acidified MRS agar as described below. MRS medium was created for favoring the growth of lactic acid bacteria, especially *Lactobacillus* sp. It is believed to disfavor the growth of the vast majority of Gram negative bacteria. However, other bacteria than lactic acid bacteria may eventually grow in MRS, and it is therefore recommendable or even necessary to check that the colonies belong to Gram positive and are catalase negative bacteria.

The lactic acid bacteria preferred herein may possibly be probiotic bacteria. The most commonly accepted definition of "probiotic" was given in 1998 by Füller, who described it as "a live microbial feed supplement which beneficially affects the host animal by improving its intestinal microbial balance". Generally, probiotics are live microorganisms. It is believed that different probiotics have different actions in the gut, and different probiotics may therefore act together to provide a beneficial effect. Other sources define probiotics as those microorganisms for which a health benefit on the human or animal has already been proven. Selection criteria for probiotics are published in: "Report of a Joint FAO/

WHO Expert Consultation on Evaluation of Health and Nutritional Properties of Probiotics in Food Including Powder Milk with Live Lactic Acid Bacteria", Food and Agriculture Organization of the United Nations and World Health Organization, 2001, Cordoba, Argentina. The advantages of the use of life bacteria have been widely described.

In recent years, the concept of "prebiotics" was introduced; prebiotics are non-digestible food components that increase the growth of specific microorganisms in the gastrointestinal tract. "Synbiotics" are compositions comprising at least one probiotic and at least one prebiotic. Such compositions are understood to encourage the growth of beneficial bacteria (e.g. the probiotics). As an illustrative example, fermented dairy products are oftentimes considered as synbiotics because they contain live bacteria and the food source needed for them. Although benefits associated with prebiotics and probiotics are favorable, researchers are cautious about drawing general conclusions because benefits vary, depending on type and amount of pre- and probiotic consumed, as well as specific combinations of specific probiotics with specific prebiotics. Thus, powerful synbiotics are based on a combination of specific strains of probiotic bacteria with carefully selected prebiotics. They can lead to an important health benefit to a mammal.

Specific probiotics, prebiotics and synbiotics have been suggested for uses in humans and selection criteria for probiotics are disclosed for example in "Report of a Joint FAO/WHO Expert Consultation on Evaluation of Health and Nutritional Properties of Probiotics in Food Including Powder Milk with Live Lactic Acid Bacteria", Food and Agriculture Organization of the United Nations and World Health Organization, 2001, Cordoba, Argentina.

The present invention uses microorganisms, bacteria in particular, which have a potential of showing a health benefit on animals, farm animals in particular. Preferably, the animal is a domestic, domesticated animal or an animal which itself is not domestic or domesticated (i.e. wild) but which belongs to the same species or genus as a domestic animal. A wild pig for example would be included in this definition since it belongs to the same species as a domestic pig. Some examples of domestic animals that can be treated include without limitation dogs, cats and other pets, horses, cattle, chicken and other poultry, swine, sheep, goats. Preferably the animal is a farm animal, and farm animals include without limitation horses, cattle, chicken and other poultry, swine, sheep, goats. More preferably, the animal is from the suborder Suina. The suborder Suina (also known as Suiformes) is a lineage of mammals that includes the pigs and peccaries of the families Suidae and Tayassuidae. Swine or pig, either wild or domestic, may be particularly preferred.

The strains which are suitable for the present invention can be identified as follows.

First Step for Arriving at the Strains of the Invention: Isolation of Single Strains In a first step, a sample containing microorganisms (preferably bacteria) is isolated. Any source of microorganisms can be suitable, which in the broadest sense can be any non-sterile sample from nature. The source may be from (domestic) animals, such as from young animals in the first 30 days of life, or from their mothers. Alternatively, the source may be from wild animals (e.g. wild boars), such as samples collected from captured wild boars. Suitable sources include colostrum from mother animals (e.g. sows), meconium samples from newborn animals (e.g. piglets), intestinal wall washes from domestic or wild animals or natural intestinal lactic acid bacteria. Microorganisms (e.g. bacteria) contained in the samples may be grown on growth media well known in the art to be suitable for growth of intestinal microorganism, e.g. MRS medium. The microorganisms may be streaked out, which will enable the isolation of single colonies. The single colonies can be picked and the respective strains further propagated in a suitable growth medium (for example the same as was used initially).

The strains of these single colonies are optionally tested by Gram staining by methods known in the art (and selected if they are Gram positive) and/or tested for the presence of Catalase activity as described above (and selected if they are Catalase negative).

Second Step of Arriving at the Strains of the Invention: In Vitro Tests

In order to be selected as useful for the present invention, a microorganism strain, originating preferably from the first step described above, must fulfil at least one of the following criteria which are first listed here and then detailed below:
 a. Activity against undesired bacteria;
 b. Acid tolerance;
 c. Bile salts tolerance;

The items a. to c. represent priority; i.e. it is most desired that criterion a. is met, second-most-desired that criteria a. and b. are met, and most preferred that all criteria a. to c. are met. The selection criteria are detailed as follows.

(i) Activity Against Undesired Bacteria

In vitro screening against undesired bacteria is done. "Undesired" are bacteria selected from the following one or more: *Salmonella* sp., *Listeria monocytogenes*, *Staphyloccocus aureus* and *Escherichia coli*. Preferably, the *Salmonella* species is *Salmonella enterica*, more preferably *Salmonella enterica* serotype *Typhimurium*.

The activity against the undesired bacteria is tested according to the spot on lawn test, which is described in the following. Liquid overnight cultures (MRS) of each strain to be tested are applied as single spots of 10 µl on MRS agar and incubated at 30° C. for 24 h in anaerobic conditions. After incubation, the plates are covered with 7 ml of semi-solid BHI agar (0.7%) inoculated with one of the undesired bacteria (1%; 1 ml overnight culture in 100 ml medium). Separate plates containing one particular strain to be tested are overlaid with one of the undesired bacteria species, respectively. Each such test is performed in triplicate. After incubation for 24 h at or near the optimal growth temperature of the undesired bacterium (which optimal growth temperature is known in the art for each of the undesired bacteria referred to herein), the samples are examined for evidence of inhibition. To that end it is first checked if an inhibition zone is present. If so, the diameter of the inhibition zone is measured optically. In events where the inhibition zone appears not exactly circular the measurement of the inhibition zone is done with a rule of measuring the inhibition zone's shortest diameter. Finally, the arithmetic mean of the triplicate experiment is determined and it is checked if the following criterium is met.

CRITERIUM: At least one of the following conditions [(i), (ii), (iii), (iv)] must be fulfilled for a strain in order to be selected as positive:

For *Salmonella*, inhibition zone 10 mm or more, for example 14 mm or more.

(ii) For *Listeria monocytogenes*, inhibition zone 9 mm or more, preferably 10 mm or more.

(iii) For *Staphyloccocus aureus*, inhibition zone 9 mm or more, preferably 10 mm or more.

(iv) For *Escherichia coli*, inhibition zone 10 mm or more, for example 18 mm or more.

9 mm or more includes 10 mm or more, 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more 10 mm or more includes 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more 26 mm or more, 27 mm or more, 28 mm or more, 29 mm or more, 30 mm or more, 35 mm or more.

14 mm or more includes 15 mm or more, 16 mm or more, 17 mm or more, 18 mm or more, 19 mm or more, 20 mm or more, 19 mm or more, 20 mm or more, 25 mm or more, 30 mm or more. 18 mm or more includes 19 or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more.

A composition comprising several strains can also be tested for the above criteria, and such composition, in order to be selected to be suitable for any of the medical uses described herein, must fulfill all of the criteria [(i), (ii), (iii), (iv)]. It can also be expected that such a composition can suitably be prepared by combining individual microorganism strains of which everyone fulfills at least one of the criteria (i), (ii), (iii), (iv); but whether this is really the case must be experimentally tested.

Alternatively, the agar well diffusion assay may be used for determining inhibition zones. This process eliminates any traces of lactic acid that could be produced in low glucose MRS broth by neutralizing cell-free supernatants. Stationary phase cultures of the species to be tested, grown under anaerobic conditions, are harvested by centrifugation (5000 g/20 min/4° C.), and the pH of the cell-free supernatant is adjusted to 6.5 with 1M NaOH. Supernatants are filter-sterilized (0.20 mm; Millipore Ltd., Hertfordshire, England). The cell-free supernatant (30 µl) is added to 7-mm diameter wells cut into agar plates inoculated with [approximately] $10^5$ colony-forming units (CFU)/ml of the undesired bacterium listed in (i), (ii), (iii), (iv). The agar plates are then incubated at 30° C. for 24 hours. The diameter of the inhibition zones around the wells is measured, and selection criteria are as indicated under (i), (ii), (iii), (iv) above, of which at least one must be fulfilled for a strain to be selected as positive.

For information: the assays above are based on what has been described by Kawai et al., 2004. Applied and Environmental Microbiology 70(5): 2906-2911; Dortu et al. 2008. Letters in Applied Microbiology, 47: 581-586; Hata et al., 2009. International Journal of Food Microbiology, 137: 94-99, Awaisheh 2009. Food Pathogens and Disease 6 (9): 1125-1132.).

(ii) Acid Tolerance

Acid can be seen as mimicking gastric juice, and tolerance thereto is tested as follows. 100 µl of an initial suspension in MRS of a 6-8×10$^8$ CFU/ml of each strain are suspended in acidified MRS (pH=3.5, or, alternatively pH=2.5) acidified upon addition of appropriate amount of 12 N HCl) and incubated 37° C. under 110 rpm agitation. Samples are tested by colony count (CFU/ml) at hour 0, 3 and 6.

CRITERIUM: The strain must be able to retain essentially the same viability (at least 50%, or at least 55%, or at least 60%, or at least 70%, or at least 75%, or at least 80%, or at least 95% CFU after the test compared to before, most preferably at least 50% CFU after the test compared to before) during 3 hours of incubation in said medium. For reference: a similar protocol is briefly described by Huang et al., International Journal of Food Microbiology 91: 253-260).

(iii) Bile Salts Tolerance

Simulation of the mammal's natural small intestine conditions

100 µl of an initial suspension in MRS of a 6-8×10$^8$ CFU/ml of a bacterial strain are suspended in simulated small intestine solution (e.g. MRS at pH=8 (pH adjusted upon addition of NaOH) and 0.45% bile extract (Bile extract, porcine. B8631-100G. SIGMA-ALDRICH)) and incubated 37° C. under 110 rpm agitation. Samples were tested by colony count (CFU/ml) at hour 1, 2 and 4.

CRITERIUM: No loss of viability (or essentially no loss of viability, i.e. preferably 50% or more CFU, such as 50%, or 60%, or 70%, or 75%, or 80%, or 95% or more CFU) after exposure to simulated small intestine juices (0, 45% bile salts, optionally at pH=8) for 4 hours. A similar protocol is briefly described by Huang et al., International Journal of Food Microbiology 91: 253-260.

Optionally, the strains that had been identified as positive by the above criteria a. to c. can also be tested for their adherence to epithelial surfaces and persistence in the animal (e.g. swine) gastrointestinal tract. It is believed that strains with good adherence properties will perform best.

Optionally, the strains that had been identified as positive by the above criteria a. to c. are additionally tested for their antibiotic resistance profile, e.g. by the Minimal antibiotic concentration test (VetMIC microplate tests) and/or a genotypic resistance test is performed by performing a PCR for different resistance genes (Egervärn of al., 2010. Antonie van Leeuwenhoek 97: 189-200). It is believed that bacteria with no antibiotic resistance (absence or inactivity/loss-of-function of resistance genes) are most suited for application to farm animals.

The lactic acid bacterium of the present invention may be selected from the following strains: CECT 8163 (AqSyn04); CECT 8165 (AqSyn06); CECT 8164 (AqSyn09); CECT 8166 (AqSyn10), CECT 8347 (AqSynJ12), CECT 8348 (AqSynJ17), CECT 8349 (AqSynJ55) and CECT 8350 (AqSynJ59). It is believed that all these strains have probiotic properties, and they may therefore be referred to as probiotics herein. The respective strains were isolated by the present inventors according to the selection criteria above. CECT refers to Spanish Type Cultures Collection, while the AqSyn numbers in brackets, which can be used synonymously for each of the strains, were allocated to the strains by the present inventors. Each bacterium was tested and found to fulfill at least one of criteria a. to c. above. When finding further strains with beneficial properties according to this invention, it may be sufficient that any such strain, in order to be selected as suitable for the present invention, fulfills at least one of the criteria a. to c. above. The invention also provides a composition comprising at least one, such as one, preferably at least two, such as two, more preferably at least three, such as three, more preferably at least four, such as four, alternatively at least five, such as five, alternatively at least six, such as six, alternatively at least seven, such as seven, alternatively at least eight, such as eight of these strains. It is believed that different strains have different actions in the gut, and different strains may therefore act together to provide a beneficial effect.

In a particular embodiment, the composition comprises at least one, such as one preferably two, such as two, more preferably the following three strains: CECT 8163 (AqSyn04); CECT 8164 (AqSyn09) and CECT 8166 (AqSyn10). In an alternative embodiment, the composition comprises the following strains: CECT 8163 (AqSyn04); CECT 8165 (AqSyn06); CECT 8164 (AqSyn09) and CECT 8166 (AqSyn10).

In an alternative embodiment, the composition comprises one or more of CECT 8163 (AqSyn04); CECT 8165 (AqSyn06); CECT 8164 (AqSyn09); CECT 8166 (AqSyn10); CECT 8347 (AqSynJ12); CECT 8348 (AqSynJ17); CECT 8349 (AqSynJ55) and CECT 8350 (AqSynJ59), such as one, two, three, four, five, six seven, eight.

In an alternative embodiment, the composition comprises at least one, such as one, preferably at least two, such as two, more preferably at least three, such as three, more preferably at least four, such as four of CECT 8347 (AqSynJ12); CECT 8348 (AqSynJ17); CECT 8349 (AqSynJ55) and CECT 8350 (AqSynJ59).

In an alternative embodiment, the composition comprises the following three strains: CECT 8347 (AqSynJ12); CECT 8348 (AqSynJ17) and CECT 8349 (AqSynJ55). In an alternative embodiment, the composition comprises the following three strains: CECT 8348 (AqSynJ17); CECT 8349 (AqSynJ55) and CECT 8350 (AqSynJ59). In an alternative embodiment, the composition comprises the following three strains: CECT 8347 (AqSynJ12); CECT 8348 (AqSynJ17); and CECT 8350 (AqSynJ59). In an alternative embodiment, the composition comprises the following three strains: CECT 8347 (AqSynJ12); CECT 8349 (AqSynJ55) and CECT 8350 (AqSynJ59). In an alternative embodiment, the composition comprises all four of CECT 8347 (AqSynJ12); CECT 8348 (AqSynJ17); CECT 8349 (AqSynJ55) and CECT 8350 (AqSynJ59).

In one embodiment of the present invention at least one of the strains comprised in the composition, such as one, and/or two, and/or three, and/or four and/or five and/or six, and/or seven and/or eight of the strains comprised in the composition, and preferably all of the strains comprised in the composition, are free from antibiotic resistance, namely they are not able to survive after exposure to the appropriate standard antibiotic treatment.

An in vitro test of minimal inhibitory concentration (MIC) aimed to evaluate antibiotic resistances may performed for all the strains suggested. The evaluated antibiotics may be the following:

Ampicillin, Vancomicin, Gentamicin, Kanamycin, Streptomycin, Eritromycin, Clindamycin, Tetracyclin and Chloranphenicol.

For the purpose of distinguishing resistant from susceptible strains, the European Food Safety Authority (EFSA) Panel on Additives and Products or Substances used in Animal Feed (FEEDAP) defines microbiological cut-off values. Microbiological cut-off values are set by studying the distribution of MICs of the chosen antimicrobials in bacterial populations belonging to a single taxonomical unit (species or genus). The part of the population that clearly deviates from the normal susceptible populations is categorised as resistant. The microbiological cut-off values that may be used for evaluating the antibiotic resistances of the strains of the present invention are the ones defined in the "Guidance on the assessment of bacterial susceptibility to antimicrobials of human and veterinary importance", EFSA Panel on Additives and Products or Substances used in Animal Feed (FEEDAP), European Food Safety Authority (EFSA), Parma, Italy. EFSA Journal 2012; 10(6):2740.

In either case "comprises" may optionally be understood in that further bacterial strains are present, or that no further bacterial strains are present. Even if no further bacterial strains are present, "comprises" may optionally mean that further other ingredients, i.e. any ingredients other than bacteria are present.

The other ingredient (or other ingredients) is not limited in any way. In a preferred aspect, at least one prebiotic compound is comprised in the composition of the invention, i.e. as other ingredient. In a very broad concept, prebiotics are all those food sources which can be metabolized by probiotics. Preferably prebiotics are non-digestible or poorly digestible by a mammal. Thus, following uptake by the mammal, the non-digestible prebiotics can pass through the small intestine and enter the large intestine to stimulate the growth of the probiotics in this compartment. Prebiotics can thus serve as a food source for probiotics. It is believed that the prebiotics, many of which are non-digestible carbohydrates, promote the growth of probiotics inside the gut. Prebiotics are naturally found for example in onions, whole grains, bananas, garlic, honey, leeks, artichokes, fortified foods and beverages, as well as dietary supplements. Prebiotics are well known in the art and when used in the present invention there is no particular limitation of the prebiotic as such. In preferred embodiments however the at least one prebiotic product in the composition is selected from the following compounds and compositions: non-digestible carbohydrates, beta-glucans, mannan-oligosaccharides, inulin, oligofructose, galactooligosaccharides (GOS), lactulose, lactosucrose, galactotriose, fructo-oligosaccaride (FOS), cellobiose, cellodextrins, cylodextrins, maltitol, lactitol, glycosilsucrose, Vitamin E or a variant thereof (wherein the variants are selected from alfa, beta, gamma, delta tocoferols, tocotrienols and tocomonoenols). Optionally, mannan-oligosaccharides and/or inulin may be preferred.

Concerning the compositions of different strains, any mixing ratio is possible. The mixing ratio is indicated in colony forming units (CFU), which are suitably determined prior to mixing the individual strains. In one embodiment, the ratios of the strains may or may not be equal, such as 1:(0,1-10):(0,1-10) for a composition of three strains, 1:(0,1-10):(0,1-10):(0,1-10) for a composition of four strains, and so forth. In another embodiment, the ratios of the strains are roughly or substantially equal, such as 1:1:1 for a composition of three strains, 1:1:1:1 for a composition of four strains, and so forth. The composition can be prepared by mixing the respective bacterial amount (as determined by colony count) of each strain to be incorporated into the composition.

The present invention also provides the use of a composition in a method of treating a human or animal. Treatment of an animal, a mammal and/or a domestic animal in particular, may be preferred. Preferably, the animal is from the suborder Suina (the suborder Suina is a lineage of mammals that includes the pigs and peccaries of the families Suidae and Tayassuidae). Swine or pig, either wild or domestic, may be particularly preferred. This also includes pigs which live in semi-wild conditions, i.e. races of domestic pigs that live most of the year outdoors and find their own food. The composition may be a composition comprising at least one of the above-described deposited strains.

The invention also provides a composition comprising lactic acid bacteria for use in a method for increasing weight of a newborn mammal, preferably a piglet. Alternatively, the composition is for use in a method for promoting growth of a newborn mammal, preferably a piglet. Alternatively, the composition is for use in a method for treating or preventing the diarrhoea caused by a bacterial infection in a newborn mammal, preferably a piglet. At least one, preferably at least two, more preferably at least three, such as four or more than four different strains of lactic acid bacteria are comprised in the composition. In the case of the composition for the use described in this paragraph, each lactic acid bacterium must fulfill at least one of the criteria a. to c. (activity against undesired bacteria; acid tolerance; bile salts tolerance) as described above. Concerning criterium a., the above-referenced minimal inhibition zone is typically observed for all of undesired bacteria (i) to (iv). Preferably, the composition should fulfill a plurality (such as a. and b.) and preferably all of the criteria (a. to c.) above. It is also possible that in said method no antibiotic is administered to the animal. Either a probiotic composition or a synbiotic composition can be used in said method (i.e. one comprising at least one prebiotic compound).

The composition of the invention composition comprises live microorganisms, preferably bacteria. In particular, said composition for use in a method for increasing weight and/or for promoting growth and/or for treating or preventing the diarrhoea caused by a bacterial infection, may comprise at least one, such as one and/or two, and/or three, and/or four, and/or five, and/or six, and/or seven, and/or eight, of the bacterial strains CECT 8163 (AqSyn04); CECT 8165 (AqSyn06); CECT 8164 (AqSyn09); CECT 8166 (AqSyn10); CECT 8347 (AqSynJ12); CECT 8348 (AqSynJ17); CECT 8349 (AqSynJ55); and CECT 8350 (AqSynJ59). In some embodiments said composition for use in a method for increasing weight and/or for promoting growth and/or for treating or preventing the diarrhoea caused by a bacterial infection is the above-described particular composition (in any embodiment described).

The composition for the use in a method for increasing weight and/or for promoting growth and/or for treating or preventing the diarrhoea caused by a bacterial infection, may be administered within the first 14 days after birth (more preferably within the first 13, or 12, or 11, or 10, or 9, or 8, or 7, or 6, or 5, or 4, or 3 or 2 days after birth and most preferably within the first 2 days after birth or within the first 1 day (24 hours) after birth.

Any route of administration is suitable, but oral administration may be preferred. Most typically, a dose is given to every animal directly into the mouth to make sure that the animal swallows the dose. Alternatively, the composition may also be provided as a food supplement, i.e. added to the daily feed of the animal.

The composition may be in any form, such as in lyophilized, liquid or nebulized form. If for example lyophilized bacteria are used for making the composition, then said preliminary composition of lyophilized bacteria may be rehydrated, e.g. with sterile isotonic saline solution or with sterile water or with sterile growth medium, so that a final composition with the desired total concentration (CFU/ml) can be obtained.

To provide for easy use, the composition may be in dosed form. For example, each dose may comprise $10^7$ or more, $10^8$ or more, $10^9$ or more, $10^{10}$ or more, $10^{11}$ or more colony forming units (CFU) of microorganisms (bacteria); a dose of $10^9$ or more may be preferred. A dose may have a volume in the range of 0.1 to 100 ml, preferably 0.2 to 50 ml, more preferably 0.5 to 20 ml, more preferably 1.0 to 10 ml, more preferably 1.5 to 5 ml, and even more preferably (substantially) 2 ml. A 2 ml dose with $10^9$ or more CFU may be particularly preferred.

Any number of doses may be administered and the skilled person can chose the length of the treatment according to the needs at the respective farm. In a particular embodiment the total number of doses administered to an animal is 10 or less, such as any number selected from the following: 1, 2, 3, 4, 5, 6, 7, 8, 9, 10, or any range combining any one of these numbers (except 10) with any one of these number, provided that the second number is higher (e.g. 1 to 3 doses for example). A total of two doses per animal may be particularly preferred.

The inventors thus provide a new use for such compositions by optionally employing the probiotic or synbiotic composition at an early life stage. In a preferred embodiment, a first dose is administered in the first 24 hours after birth and a second dose is administered in the subsequent 24 hours. Optionally, these are the only two doses. In another option, further doses are administered in the following.

The composition of the invention is particularly suitable for treating or preventing a condition in a mammal, such as a bacterial infection or dysbiosis. The infection may be or include an infection of the digestive tract. Such infection may be caused by any bacterium, such as e.g. *Escherichia coli*, alone or in combination with *Clostridium perfringens* or with *Clostridium difficile*. Other causative factors may include *Salmonella, Listeria monocytogenes, Staphylococcus aureus*. In some embodiments the condition may be selected from diarrhoea due to bacterial infections (including collibacilosis), *Clostridium difficile* newborn diarrhoea, *Clostridium perfringens* A and C type. Streptococcal meningitis may also be treated. It is also possible to administer the composition to animals suffering from diarrhoea or being at a risk of suffering from diarrhoea, even if a (bacterial) infection has not (yet) been proven to be the causative factor for said diarrhoea. Animals being at a risk of suffering from diarrhoea can be seen as those animals living on (or born on) premises on which diarrhoea had been observed during the last 12 months, 6 months, 3 months or 1 month.

The inventor's results confirm the advantageous effect of the use of the products and compositions of the invention. As shown in the below proof of concept examples, the mortality percentage was clearly lower than other weeks with just routine antibiotic management (see Examples). Thus, preferably the composition of the invention is administered to animals which are not treated at the same time with antibiotic(s).

The invention also provides a microorganism, preferably a bacterium, and more preferably a lactic acid bacterium. The lactic acid bacterium is ideally selected from the following strains: CECT 8163 (AqSyn04); CECT 8165 (AqSyn06); CECT 8164 (AqSyn09); CECT 8166 (AqSyn10), CECT 8347 (AqSynJ12); CECT 8348 (AqSynJ17); CECT 8349 (AqSynJ55) and CECT 8350 (AqSynJ59), which were all deposited with CECT.

The present application comprises the following items:

1. A composition comprising one or more strains of microorganisms for use in a method for increasing weight of a newborn mammal (preferably a piglet), wherein each strain fulfills at least the following condition a, and preferably both conditions a and b, and most preferably all conditions a., b. and c.:

a. has at least one of the following antimicrobial activities, as evidenced by inhibition zones determined by the spot on lawn assay: (i) 14 mm or more inhibition zone for *Salmonella*, (ii) 9 mm or more inhibition zone for *Listeria monocytogenes*, (iii) 9 mm or more inhibition zone for *Staphyloccocus aureus*, (iv) 18 mm or more inhibition zone for *Escherichia coli*;
b. is able to retain essentially the same viability during 3 hours of incubation at pH 2.5;
c. is able to retain essentially the same viability during 4 hours of incubation in presence of 0.45% bile extract and pH=8.

2. A lactic acid bacterium selected from the following strains:
a. a strain deposited at Spanish Type Cultures Collection with deposit number CECT 8163 (AqSyn04);
b. a strain deposited at Spanish Type Cultures Collection with deposit number CECT 8165 (AqSyn06);
c. a strain deposited at Spanish Type Cultures Collection with deposit number CECT 8164 (AqSyn09); and
d. a strain deposited at Spanish Type Cultures Collection with deposit number CECT 8166 (AqSyn10).

3. A composition comprising at least one, preferably at least two, more preferably at least three, more preferably all bacterial strains of item 2.

4. The composition of item 3 comprising or consisting of the following three strains:
i. the strain deposited at Spanish Type Cultures Collection with deposit number CECT 8163 (AqSyn04);
ii. the strain deposited at Spanish Type Cultures Collection with deposit number CECT 8164 (AqSyn09)
iii. the strain deposited at Spanish Type Cultures Collection with deposit number CECT 8166 (AqSyn10).

5. The composition of item 4 comprising or consisting of all four strains of item 1.

6. The composition of any one of items 3 to 5, additionally comprising at least one prebiotic product.

7. The composition of item 6 wherein the at least one prebiotic product is selected from the following compounds and compositions: beta-glucans, mannan-oligosaccharides, inulin, oligofructose, galactooligosaccharides (GOS), lactulose, lactosucrose, galactotriose, fructo-oligosaccaride (FOS), cellobiose, cellodextrins, cylodextrins, maltitol, lactitol, glycosilsucrose, Vitamin E or a variant thereof (wherein the variants are selected from alfa, beta, gamma, delta tocoferols, tocotrienols and tocomonoenols) whereby mannan-oligosaccharides and/or inulin are preferred.

8. The composition according to any of items 3 to 7 for use in a method of treating a human or animal, which preferably is a mammal and/or a domestic animal, and more preferably a pig.

9. A composition for the use according to item 1, wherein the composition is the composition according to items 3 to 7.

10. The composition for the use according to item 1 or 9, wherein the composition is administered within the first 14 days after birth (more preferably within the first 13, 12, 11, 10, 8, 7, 6, 5, 4, 3 days after birth and most preferably within the first two days after birth.

11. The composition for use according to any one of items 1 or 9 to 10 for oral administration.

12. The composition for use according to any one of items 1 or 9 to 11 which is in lyophilized, liquid or nebulized form.

13. The composition for use according to any one of items 1 or 9 to 12, wherein the composition is provided in dosaged form, and wherein each dosage comprises $10^9$ or more colony forming units (CFU).

14. The composition for use according to item 13 for administration in two doses.

15. The composition for use according to item 14 wherein the first dose is administered in the first 24 hours after birth and the second dose is administered in the subsequent 24 hours.

16. The composition for use according to any one of items 1 or 9 to 15 for treating or preventing a bacterial infection, such as diarrhoea due to bacterial infections (including collibacilosis), *Clostridium difficile* newborn diarrhoea, *Clostridium perfringens* A and C type.

Material and Methods

MRS Medium: MRS Medium recipe was prepared according to the recipe obtained from Spanish Collection of Type Cultures (CECT; www.cect.org) as follows: Peptone 10.0 g, Beef extract 10.0 g, Yeast extract 5.0 g, Glucose 20.0 g, Ammonium citrate 2.00 g, Sodium acetate 5.00 g, MgSO4.7H2O 0.20 g, MnSO4.H2O 0.05 g, $K_2HPO_4$ 2.00 g, [Agar powder (only for solid media) 15 g,] Distilled water 1 L.

BHI (Brain Heart Infusion) Medium recipe was prepared according to the recipe obtained from Spanish collection of type cultures (CECT; www.cect.org) as follows: Calf brain infusion solids 12.5 g, Beef heart infusion solids 5.0 g, proteose peptone 10.0 g, Glucose 2.0 g, NaCl 5.0 g, HNa2PO4 2.5 g, Distilled water 1L, [Agar powder (only for solid media) 15 g].

Antibiotic treatment: Typically, each pig farm treats newborn piglets with antibiotics and possibly an iron supplement. Generally each pig farm has a different "standard" treatment for their animals (they usually inject an antibiotic dose and iron supplementation by birth). In the experiments below, the standard treatment of the respective farms was used. Antibiotics are generally also used sporadically by diarrhoea, limps, respiratory symptoms and many other facts daily without a full established protocol in piglets.

EXAMPLES

Example 1 A

Origin of the Strains

Bacterial strains were isolated and identified as follows.
The isolation of CECT 8163 (AqSyn04); CECT 8165 (AqSyn06); CECT 8164 (AqSyn09) and CECT 8166 (AqSyn10) bacterial strains was made from colostrum from sows and meconium samples from newborn piglets. The sampling took place in high sanitary quality swine farms in Spain.

Samples were grown aerobically and anaerobically in De Man, Rogosa, Sharpe (MRS) agar plates for 24 hours at 37° C., and Gram positive, Catalase negative colonies of different morphologies were isolated. All colonies belonged to bacterial strains. More precisely, 61 different bacterial strains were isolated. Each one was amplified by PCR using PCR primers targeting the 16S/23S rRNA spacer region as described by Berthier and Ehrlich, 1998. FEMS Microbiology Letters 161: 97-106.

After amplification and electrophoresis, clearly differentiated bands were purified and sequenced. The different PCR patterns are shown in FIG. 1. By sequencing the strains were allocated to several bacterial species.

1.1 Characterisation of the Strains

Without wishing to be bound to a particular theory, it is believed that substantial strain differences may exist. In order to differentiate strains of the same species an API 50

CH test (Biornerieux, REF 50 300) was performed according to the manufacturer's instructions in order to describe carbohydrate fermentation patters of the substrates, which confirms differences between strains of the same species.

From 61 strains, 10 different groups could be observed by carbohydrate fermentation patterns, confirming the presence of 10 different strains. One of each group was taken as example and subjected to the following in vitro methods The 10 strains belonged to the species *Lactobacillus reuteri* and *Enterococcus faecium*.
1. *Lactobacillus reuteri*
2. *Lactobacillus reuteri*
3. *Lactobacillus reuteri*
4. *Lactobacillus reuteri* (AqSyn04)
5. *Lactobacillus reuteri*
6. *Lactobacillus reuteri* (AqSyn06)
7. *Enterococcus faecium*
8. *Enterococcus faecium*
9. *Enterococcus faecium* (AqSyn09)
10. *Enterococcus faecium* (AqSyn10)

These 10 strains were further tested in order to check their possible use in improving animal (swine's in particular) health, see following section 1.2).

1.2 Selection of the Strains

The 10 strains identified as described in section 1.1 were further tested. It was hypothesized that a combination of antimicrobial and tolerance criteria could help to find suitable strains among the previously strains. Thus, each of the strains separately was subjected to each of the tests a. to c. described above under "selection in vitro tests".

The diligent work of the present inventors showed that criteria a. to c., described above under "selection in vitro tests", are suitable for identifying strains that are suitable for the present invention. Thus, the strains were tested according to said criteria a. to c. The in vitro tests revealed four strains with particularly beneficial properties. The results are listed below.

and two *Enterococcus faecium* (AqSyn09, AqSyn10) were identified. [Results for the remaining 6 strains, i.e. the one that did not meet at least one of the criteria a. to c., are not shown in the above Table].

A composition of these strains was prepared therefrom as described in Example 2 A.

Example 1 B

Origin of the Strains

Bacterial strains were isolated and identified as follows.

The isolation of CECT 8347 (AqSynJ12); CECT 8348 (AqSynJ17); CECT 8349 (AqSynJ55) and CECT 8350 (AqSynJ59) bacterial strains was made from intestinal wall washes of wild boar intestine.

Samples were grown aerobically and anaerobically in De Man, Rogosa, Sharpe (MRS) agar plates for 24 hours at 37° C., and Gram positive, Catalase negative colonies of different morphologies were isolated. All colonies belonged to bacterial strains. More precisely, 61 different bacterial strains were isolated. Each one was amplified by PCR using PCR primers targeting the 16S/23S rRNA spacer region as described by Berthier and Ehrlich, 1998. FEMS Microbiology Letters 161: 97-106.

After amplification and electrophoresis, clearly differentiated bands were purified and sequenced. By sequencing the strains were allocated to several bacterial species.

1.1 Characterisation and Selection of the Strains
1. *Lactobacillus fermentum* (AqSynJ12)
2. *Lactobacillus reuteri* (AqSynJ17)
3. *Lactobacillus mucosae* (AqSynJ55)
4. *Lactobacillus plantarum* (AqSynJ59)

In vitro tests following criteria a. to c., described above under "selection in vitro tests", revealed four strains with

TABLE

Results of in vitro tests:

| | AqSyn04 | AqSyn06 | AqSyn09 | AqSyn10 |
|---|---|---|---|---|
| a. (i) *Salmonella enterica* serotype *Typhimurium* inhibition zone [mm] | 17 | 14 | 17 | 17 |
| a. (ii) *Listeria monocytogenes* inhibition zone [mm] | 12 | 9 | 23 | 17 |
| a. (iii) *Staphyloccocus aureus* inhibition zone [mm] | 9 | 9 | 11 | 13 |
| a. (iv) *Escherichia coli* inhibition zone [mm] | 21 | 18 | 27 | 24 |
| b. acid tolerant (yes/no) | yes | yes | yes | yes |
| c. bile salt tolerant (yes/no) | yes | yes | yes | yes |

As can be seen in the above Table, after said in vitro tests, four strains (two *Lactobacillus reuteri* (AqSyn04, AqSyn06)

particularly beneficial properties. The results are listed below."

| | AqSynJ12 | AqSynJ17 | AqSynJ55 | AqSynJ59 |
|---|---|---|---|---|
| a. (i) *Salmonella enterica* serotype *Typhimurium* inhibition zone [mm] | 15 | 11 | 14 | 13 |
| a. (ii) *Listeria monocytogenes* inhibition zone [mm] | 13 | 10 | 15 | 13 |
| a. (iii) *Staphyloccocus aureus* inhibition zone [mm] | 10 | 10 | 9 | 9 |
| a. (iv) *Escherichia coli* inhibition zone [mm] | 18 | 16 | 20 | 21 |
| b. acid tolerant (yes/no) | yes | yes | yes | yes |
| c. bile salt tolerant (yes/no) | yes | yes | yes | yes |

As can be seen in the above Table strains from wild boars fulfil the selection criteria. Moreover, the above-identified strains are free from antibiotic resistance.

An in vitro test of minimal inhibitory concentration (MIC) aimed to evaluate antibiotic resistances was performed for the above strains (AqSynJ12, AqSynJ17, AqSynJ55, AqSynJ59). The evaluated antibiotics were the following:

Ampicillin, Vancomicin, Gentamicin, Kanamycin, Streptomycin, Eritromycin, Clindamycin, Tetracyclin and Chloranphenicol.

The microbiological cut-off values that were used for evaluating the antibiotic resistances of the strains of the present invention are the ones defined in the "Guidance on the assessment of bacterial susceptibility to antimicrobials of human and veterinary importance", EFSA Panel on Additives and Products or Substances used in Animal Feed (FEEDAP), European Food Safety Authority (EFSA), Parma, Italy. EFSA Journal 2012; 10(6):2740.

A composition of these strains was prepared therefrom as described in Example 2 B (compositions D and E).

Example 2 A

Preparation of a Probiotic Composition According to the Invention and of a Synbiotic Composition According to the Invention Each of the strains AqSyn04, AqSyn06, AqSyn09, AqSyn10 was grown in MRS broth culture by fermentation, harvested and lyophylized. Viability of the final product was checked by colony count. Compositions were prepared containing all four of these strains upon optional addition of prebiotic compounds. The following compositions were prepared:

Composition A: ($2.5 \times 10^8$ CFU of Each Strain in 2 ml)

| Components | Quantity per 2 ml dose |
|---|---|
| AqSyn04 Lactobacillus reuteri | 0.0035 g |
| AqSyn06 Lactobacillus reuteri | 0.0035 g |
| AqSyn09 Enterococcus faecium | 0.0016 g |
| AqSyn10 Enterococcus faecium | 0.00029 g |

All strains were used in lyophilized form. Composition A can be seen as probiotic.

Composition B: ($2.5 \times 10^8$ CFU of Each Strain in 2 ml)

| Components | Quantity per 2 ml dose (g) |
|---|---|
| AqSyn04 Lactobacillus reuteri | 0.0035 |
| AqSyn06 Lactobacillus reuteri | 0.0035 |
| AqSyn09 Enterococcus faecium | 0.0016 |
| AqSyn10 Enterococcus faecium | 0.00029 |
| Inulin | 0.01 |
| β-glucans and MOS | 0.01 |
| Skim milk powder | 0.02 |

All strains were used in lyophilized form. Composition B can be seen as synbiotic.

Further, a Composition C was prepared, which contained only three of the four bacterial strains (AqSyn04, AqSyn09, AqSyn10), as follows.

Composition C: ($3.3 \times 10^8$ CFU of Each Strain in 2 ml)

| Components | Quantity per 2 ml dose (g) |
|---|---|
| AqSyn04 Lactobacillus reuteri | 0.0047 |
| AqSyn09 Enterococcus faecium | 0.0021 |
| AqSyn10 Enterococcus faecium | 0.00038 |
| Inulin | 0.01 |
| β-glucans and MOS | 0.01 |
| Skim milk powder | 0.02 |

All strains were used in lyophilized form. Composition C can be seen as synbiotic.

The compositions were prepared by mixing the same bacterial amount (as determined by colony count (respective values in g indicated above) of each strain to be incorporated into the composition, the indicated further ingredients were added (e.g. composition B, composition C), and the so obtained respective composition was rehydrated with isotonic saline solution, so that a final composition containing $10^9$ CFU (total of all strains contained therein) in a 2 ml dose was obtained.

Example 2 B

Preparation of a Probiotic Composition According to the Invention and of a Synbiotic Composition According to the Invention Each of the strains AqSynJ12, AqSynJ17, AqSynJ55, AqSynJ59 was grown in MRS broth culture by fermentation, harvested and lyophilized. Viability of the final product was checked by colony count. Compositions were prepared containing all four of these strains upon optional addition of prebiotic compounds. The following compositions were prepared:

Composition D: ($2.5 \times 10^8$ CFU of Each Strain in 2 ml)

| Components | Quantity per 2 ml dose |
|---|---|
| AqSynJ12 Lactobacillus fermentum | 0.173 g |
| AqSynJ17 Lactobacillus reuteri | 0.04 g |
| AqSynJ55 Lactobacillus mucosae | 0.008 g |
| AqSynJ59 Lactobacillus plantarum | 0.002 g |

All strains were used in lyophilized form. Composition D can be seen as probiotic.

Composition E: ($2.5 \times 10^8$ CFU of Each Strain in 2 ml)

| Components | Quantity per 2 ml dose (g) |
|---|---|
| AqSynJ12 Lactobacillus fermentum | 0.173 g |
| AqSynJ17 Lactobacillus reuteri | 0.04 g |
| AqSynJ55 Lactobacillus mucosae | 0.008 g |
| AqSynJ59 Lactobacillus plantarum | 0.002 g |
| Inulin | 0.01 |
| β-glucans and MOS | 0.01 |
| Skim milk powder | 0.02 |

All strains were used in lyophilized form. Composition E can be seen as synbiotic.

Example 3

Administration to Piglets without Administration of Antibiotics (First Proof of Concept)

The first proof of concept was carried out in a swine farm next farm located in the province of Zamora (Spain) with 2400 sows and chronic diarrhoeal problems in newborn piglets. Seven litters (78 piglets) received composition A (see Example 2 A), and another seven litters (81 piglets) were kept as control, as follows.

The piglets to which composition A was administered received one dose (see Example 2 A) daily from birth to the $14^{th}$ life day without antibiotic treatment.

The treatment of the control group was an IM injection of 1 ml of a commercial product containing 150 mg of amoxicillin and 40,000 UI of gentamicin. The diarrhoeic piglets in this group were receiving this treatment once per day during the days they showed diarrhoea.

|  | composition A | Antibiotic treatment (control) |
|---|---|---|
| Mean diarrhoeal time (days) | 3.14 | 5.29 |
| Mean daily gain (from day 0 to day 9) (g) | 178 | 141 |
| Mean daily gain by weaning (23 days) (g) | 225 | 170 |
| Mean weight by weaning (kg) | 6.70 | 5.47 |

Results of this first proof of concept appeared quite remarkable, showing an unexpected efficacy of the treatment of the invention. In sight of these results the inventors assumed not only the expected effect in pathogen flora but also a stimulation of the piglet's natural immune system. Without wishing to be bound to a particular theory, it can be understood that the administered composition had direct effect on digestive pathogens and probably on the natural response of the piglets against these digestive infections.

Example 4

Administration to Piglets in Different Dosage Regimes (Second Proof of Concept)

This experiment was carried out in Zamora (Spain) in the same farm as Example 3. Briefly, the inventors aimed at demonstrating the influence of composition A on the newborn piglet's innate immune system. Administration at different stages of a piglet's early life was also investigated. It is understood that in early piglet's life, the animal's flora is still immature.

Composition A was given to seven litters (65 piglets) at the day of birth, a second group of seven litters (84 piglets) received the composition A at first and second life days (any antibiotic application) and a third group of seven litters (80 piglets) was taken as control, as in Example 3. It is important to note that only the control group received antibiotic treatment while the groups receiving composition A were without any antibiotic application. The inventors demonstrate that similar weight gain can be reached as in the control group.

|  | 1 dose composition A | 2 doses composition A | Antibiotic treatment (control) |
|---|---|---|---|
| Mean diarrhoeal time (days) | 4.1 | 4.3 | 1 |
| Mean daily gain by weaning (19-22 days) (g) | 147 | 198 | 187 |
| Mean weight by weaning (kg) | 5.47 | 5.36 | 5.58 |
| Mortality (%) | 4 (6.15) | 1 (1.19) | 4 (5) |

The results show that administration of two doses is beneficial. In particular, double application at very early stages after the piglet's birth can protect the animals against digestive diseases without use of antibiotics, and mortality can be reduced.

A further important observation at this point is that the probiotic administration that was tested is at least equally effective as the treatment with antibiotics in terms of productivity.

Example 5

Administration to Piglets and Influence on the Immune System (Third Proof of Concept)

The third proof of concept was carried out in a farm located in the province of Murcia. The farm had 2.400 sows and problems of diarrhoea in piglets just after birth. These digestive problems were diagnosed as produced by *Escherichia coli* and *Clostridium difficile*.

Usual treatment of the piglets in this farm (control piglets in this experiment) was an injection of 100 mg of tulathromycin just after birth. Afterwards, the piglets that had diarrhoea during lactation were also orally treated with spiramycin (25 mg/kg live weight) and colistin (5 mg/kg live weight) once per day during the days they had diarrhoea.

In this experiment the composition A was administrated twice in 29 litters, i.e. (1) just after birth and (2) on the second life day, without antibiotic treatment. 34 litters were handled as usual farm's procedures.

TABLE

| Productive index by weaning | | |
|---|---|---|
|  | Composition A | Usual treatment (Control) |
| Litters | 29 | 34 |
| Mean days with diarrhoea per litter | 1.51 | 2.88 |
| Mortality per litter | 0.68 | 1.08 |

This proof of concept certified the possibility of improving the management of early digestive disturbances in newborn piglets, particularly without the use of antibiotics.

Example 6

Administration to Piglets and Influence on the Immune System (Fourth Proof of Concept)

The next proof of concept was aimed to test the product as regular performance in farm's routine. This experiment took place in the region of Huesca in a 5.500 sows farm. Due to logistical facts it was not possible to keep a control group. Composition B was given to all piglets born in a certain week (week 13 of the year 2012), comparing the productive indicators with the weeks below and after the experiment. On this farm, the usual treatment of the piglets with diarrhoea was the administration during three days of 1 ml per day of a commercial product containing 100 mg of ampicillin and 250,000 IU methanesulphonate sodium collistin Results of productive indicators; composition B was administered in the $13^{th}$ week.

|  | Weeks | | | | | |
| --- | --- | --- | --- | --- | --- | --- |
|  | 10 | 11 | 12 | 13 | 14 | 15 |
| Litters | 236 | 240 | 236 | 240 | 240 | 237 |
| Weaned piglets | 2530 | 2558 | 2574 | 2601 | 2597 | 2558 |
| Number of weaned piglets per sow | 10.72 | 10.66 | 10.91 | 10.84 | 10.8 | 10.9 |
| % Mortality | 10.2 | 9.32 | 13 | 9.1 | 13.1 | 11.3 |
| Days of lactation | 20.67 | 20.7 | 21.9 | 21.5 | 21.93 | 21.15 |
| Weaning weight (kg) | 6.1 | 6.2 | 5.8 | 6.2 | 6 | nd |
| Veterinary's comments |  |  |  | (A) |  |  |

(A) Diarrhoeal cases were observed by 80% of primipara sows (as usual without treatment with composition B) and some of multipara sows. Piglets were from 3 to 5 days old. All diarrhoea cases disappeared without antibiotic treatment.

The inventor's results confirm the advantageous effect of the use of the products and compositions of the invention. The mortality percentage was clearly lower than other weeks with just routine antibiotic management.

Example 7

In vivo experiments with composition E were performed in a farm in Zaragoza (Spain) with 1.200 hyper prolific mothers (average of 14 piglets born alive per delivery) and 56 births per week (784 piglets per week), which aims to grow piglets to 20 kg to then supply other farms, with periodic problems of diarrhoea in the lactating phase in piglets less than 1 week of life. The farmer managed the piglets in a standard way and administered the product (composition E above) at birth and at the second day of life to all the litters. Results of the treatment with composition E were similar to those obtained with compositions A, B and C.

The invention claimed is:

1. A method for treating diarrhea in a newborn mammal, comprising administering to said mammal a composition comprising a *Lactobacillus plantarum* strain deposit number CECT 8350 (AqSynJ59) deposited at the Spanish Type Cultures Collection wherein the composition is administered within the first 14 days after birth, thereby treating said diarrhea in said mammal.

2. The method according to claim 1, wherein the diarrhea is caused by a bacterial infection.

3. The method according to claim 1, wherein the mammal belongs to the suborder Suina, or is a dog, a cat, a horse, cattle, a sheep, or a goat.

4. The method according to claim 3, wherein the mammal is a piglet or a dog.

5. The method according to claim 1, wherein the composition is administered within the first 7 days after birth of the mammal.

6. The method according to claim 5, wherein the composition is administered within the first 2 days after birth of the mammal.

7. The method according to claim 1, wherein the composition additionally comprises at least one prebiotic product selected from the group consisting of: beta-glucan, mannan-oligosaccharide, inulin, oligofructose, galactooligosaccharide (GOS), lactulose, lactosucrose, galactotriose, fructo-oligosaccharide (FOS), cellobiose, cellodextrin, cyclodextrin, maltitol, lactitol, glycosilsucrose, and Vitamin E or a variant thereof.

8. The method according to claim 1, wherein the composition is administered orally.

9. A method for promoting weight gain in a newborn mammal, comprising administering to said mammal a composition comprising a *Lactobacillus plantarum* strain deposit number CECT 8350 (AqSynJ59) deposited at the Spanish Type Cultures Collection, wherein the composition is administered within the first 14 days after birth, thereby promoting weight gain in said mammal.

10. The method according to claim 9, wherein the mammal belongs to the suborder Suina, or is a dog, a cat, a horse, cattle, a sheep, or a goat.

11. The method according to claim 10, wherein the mammal is a piglet or a dog.

12. The method according to claim 9, wherein the composition is administered within the first 7 days after birth of the mammal.

13. The method according to claim 12, wherein the composition is administered within the first 2 days after birth of the mammal.

14. The method according to claim 9, wherein the composition additionally comprises at least one prebiotic product selected from the group consisting of: beta-glucan, mannan-oligosaccharide, inulin, oligofructose, galactooligosaccharide (GOS), lactulose, lactosucrose, galactotriose, fructo-oligosaccharide (FOS), cellobiose, cellodextrin, cyclodextrin, maltitol, lactitol, glycosilsucrose, and Vitamin E or a variant thereof.

15. The method according to claim 9, wherein the composition is administered orally.

16. A method for promoting growth of a newborn mammal, comprising administering to said mammal a composition comprising a *Lactobacillus plantarum* strain deposit number CECT 8350 (AqSynJ59) deposited at the Spanish Type Cultures Collection, wherein the composition is administered within the first 14 days after birth, thereby promoting growth of said mammal.

17. The method according to claim 16, wherein the mammal belongs to the suborder Suina, or is a dog, a cat, a horse, cattle, a sheep, or a goat.

18. The method according to claim 17, wherein the mammal is a piglet or a dog.

19. The method according to claim 16, wherein the composition is administered within the first 7 days after birth of the mammal.

20. The method according to claim 19, wherein the composition is administered within the first 2 days after birth of the mammal.

21. The method according to claim 16, wherein the composition additionally comprises at least one prebiotic product selected from the group consisting of: beta-glucan, mannan-oligosaccharide, inulin, oligofructose, galactooligosaccharide (GOS), lactulose, lactosucrose, galactotriose, fructo-oligosaccharide (FOS), cellobiose, cellodextrin, cyclodextrin, maltitol, lactitol, glycosilsucrose, and Vitamin E or a variant thereof.

22. The method according to claim 16, wherein the composition is administered orally.

23. A method for reducing mean diarrhoeal time in a population of newborn mammals as compared to the mean diarrhoeal time in a population of newborn mammals treated with an antibiotic, comprising administering to said mammals a composition comprising a *Lactobacillus plantarum* strain deposit number CECT 8350 (AqSynJ59) deposited at the Spanish Type Cultures Collection, wherein the composition is administered within the first 14 days after birth, thereby reducing mean diarrhoeal time in said population of said mammals.

24. A method for reducing mortality in a population of newborn mammals as compared to mortality in a population of newborn mammals treated with an antibiotic, comprising administering to said mammals a composition comprising a *Lactobacillus plantarum* strain deposit number CECT 8350 (AqSynJ59) deposited at the Spanish Type Cultures Collection, wherein the composition is administered within the first 14 days after birth, thereby reducing mortality in said population of said mammals.

\* \* \* \* \*

UNITED STATES PATENT AND TRADEMARK OFFICE
CERTIFICATE OF CORRECTION

PATENT NO. : 10,265,350 B2
APPLICATION NO. : 14/430962
DATED : April 23, 2019
INVENTOR(S) : Rubio Nistal et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Tenth Day of December, 2019

Andrei Iancu
*Director of the United States Patent and Trademark Office*